United States Patent [19]

Cavazza

[11] Patent Number: 4,771,075
[45] Date of Patent: Sep. 13, 1988

[54] USE OF ACETYL L-CARNITINE FOR THE THERAPEUTICAL TREATMENT OF SHOCK CONDITIONS

[75] Inventor: Claudio Cavazza, Rome, Italy

[73] Assignee: Sigma-Tau Industrie Farmaceutiche Riunite S.p.A., Rome, Italy

[21] Appl. No.: 915,501

[22] Filed: Oct. 6, 1986

[30] Foreign Application Priority Data

Oct. 14, 1985 [IT] Italy .............................. 48663 A/85

[51] Int. Cl.$^4$ .......................................... A61K 31/205
[52] U.S. Cl. ................................................... 514/556
[58] Field of Search ......................................... 514/556

[56] References Cited

PUBLICATIONS

Chem. Abst. 107–(1987) 33205(b).

Primary Examiner—Stanley J. Friedman
Attorney, Agent, or Firm—Ladas & Parry

[57] ABSTRACT

Intravenous administration of a bolus of 3–5 grams of acetyl L-carnitine, followed by 3–5 grams of acetyl L-carnitine via slow infusion in about 12 hours, dramatically restore to normal the arterial pressure and respiratory frequency of a patient in a severe state of shock.

3 Claims, No Drawings

USE OF ACETYL L-CARNITINE FOR THE THERAPEUTICAL TREATMENT OF SHOCK CONDITIONS

The present invention relates to a novel therapeutical utilization of acetyl L-carnitine and its pharmacologically acceptable salts for the treatment of shock conditions.

Previous therapeutical uses of acetyl L-carnitine are already known. For instance, the U.S. Pat. No. 4,194,006 discloses the use of acetyl carnitine in the therapeutical treatment of myocardial arrhythmias and ischemias. The U.S. Pat. No. 4,343,816 discloses the use of acetyl carnitine in the therapeutical treatment of functional peripheral vascular diseases of arteries, such as Reynaud's disease and acrocyanosis. The U.S. Pat. No. 4,346,107 discloses the therapeutical effectiveness of acetyl carnitine in the treatment of patients suffering from impaired cerebral metabolism as it occurs in senile and pre-senile dementia and Alzheimer's disease. There is no relationship at all, however, between the already known therapeutical utilizations of acetyl L-carnitine and the novel utilization which is the subject matter of the present invention.

This will appear more evident from the description which follows wherein a tentative biochemical explanation of acetyl L-carnitine effectiveness in shock conditions is illustrated.

It is well-known that shock is a clinical condition essentially characterized by an insufficient tissue perfusion, with usually severe hypotension which, if untreated, is generally fatal. Shock may be brought about by different causes, such as serious hemorrhages, cranial trauma, dangerous cardiac insufficiency as in certain myocardial infarctions, anaphylactic reactions, etc.

Therapy at present in actual use is not suited for all kinds of shock conditions and frequently turns out to be unsatisfactory.

Generally, in all shock conditions, the trend is to restore blood volume by means of blood, plasma, saline or glucose solutions or plasma substituents infusion, and to administer oxygen.

However, in severe shock conditions, said treatment is usually insufficient if not even counteracting. In fact, in cardiogenic shock, infusion of liquids would overload the heart, whose function is already seriously impaired because of the inadequate myocardial contractility.

Vasoconstrictor drugs, such as noradrenaline, adrenaline, metaraminol, mephentermine, which are administered in order to increase pressure, often bring about the opposite effect, since, in shock conditions (barring neurogenic shock) a severe sympathetic reflex vasoconstriction is present already, whereby tissue perfusion would be further impaired.

On the contrary, administration of drugs such as dopamine, dobutamine, isoproterenol, glucagon, etc. which improve cardiac inotropism without substantially increasing the peripheral resistances, is preferred, particularly in case of cardiogenic shock.

On the other hand, in some instances, administration of vasodilator drugs such as nitroprussiate and alpha-blockers may be convenient, in order to improve tissue perfusion.

Although corticosteroids are widely used in the treatment of shock, no convincing proofs are available which could support the effectiveness of said drugs.

Recently, the effectiveness of naloxone in different models of shock has been also studied. Although naloxone turned out to be effective in restoring blood pressure to normal values, it is absolutely contra-indicated in overdose-induced shock. It is in fact known that naloxone administration to drug addicts is followed by a typical abstinence syndrome.

Now it has been surprisingly found that the use of acetyl L-carnitine and its pharmacologically acceptable salts is dramatically effective in the therapeutic treatment of shock conditions (hypovolemic, cardiogenic, traumatic, toxic and anaphylactic shocks), cardiovascular collapse, acute hypotension and respiratory insufficiency, independently from the traumatic, psychogenic, toxic and drug overdose causes.

Therefore, in accordance with the present invention, acetyl L-carnitine and its pharmacologically acceptable salts are used for producing a pharmaceutical composition effective for the therapeutical treatment of shock conditions.

In practice, a patient in a state of shock is administered a bolus of 3-5 grams of acetyl L-carnitine. Preferably, following the administration of the acetyl L-carnitine bolus, the patient is further administered 3-5 grams of acetyl L-carnitine via slow infusion over a period of about 12 hours.

It is apparent that in the light of the therapeutical use according to the present invention the most suitable pharmaceutical compositions are those compositions which are apt to be administered via the parenteral route and which in unit dosage form comprise from about 500 to about 1,500 mg of acetyl L-carnitine and a pharmacologically acceptable excipient.

An example of such suitable pharmaceutical compositions is an adjectable vial which comprises:
Lyophilized ingredient
    acetyl L-carnitine.HCl: mg 586 (corresponding to 500 mg of inner salt)
Solvent
    water for injections: ml 5

The results of two series of clinical cases are hereinbelow illustrated; in each series the results are expressed as dead patients/treated patients ratio.

In addition to the control group and the group of the patients treated according to the present invention, also a group of patients treated with a bolus of L-carnitine and a group of patients treated with a bolus of L-carnitine followed by L-carnitine infusion, were included in the first series.

The results thus obtained show the uneffectiveness of L-carnitine in reversing shock conditions. In the second series the illustrated results refer to a control group and a group of patients treated according to the invention.

For each group, the admission criteria were as follows:
(1) systolic pressure lower than 90 mmHg or lower than 30% of patient's normal pressure;
(2) urine volume lower than 20 ml/hour;
(3) severe metabolic acidosis;
(4) weakened sensorial functions.

Each patient of both the control group and treated group received a basal treatment as hereinbelow indicated. The controls received the basal treatment only.

| Therapy | Septic shock | Cardiogenic shock |
|---|---|---|
| Alkalizers | NaHCO$_3$ till adjustment of two thirds of negative electrolytic balance | NaHCO$_3$ till adjustment of two thirds of negative electrolytic balance |
| Antacids | Cimetidine, 1 vial i.v. × 4 | Cimetidine, 1 vial i.v. × 4 |
| Antibiotics | According to the bacteria involved | Not considered |
| Sedatives and analgesics | On physician's advice | On physician's advice |
| Corticosteroids | Solu-Medrol, 30 mg/kg i.v. q. 6 hrs (for the first 12 hrs) | Not considered |
| Diuretics | Mannitol, 25 g on admission and q. 12 hrs thereafter | Furosemide, 40-60 mg i.v. following haemodynamic evaluation |
| | Fast volumetric restitution with blood, dextrane and Ringer lactate | Volumetric restitution according to Gunnar and Loeb |
| Vasoactive drugs | According to haemodynamic evaluation | According to haemodynamic evaluation |
| Cardiotonics | Cedilanid, 1 vial i.v. q. 12 hrs | Not considered |

| | 1st series | |
|---|---|---|
| | dead/treated | |
| | cardiogenic shock | septic shock |
| Controls | 4/4 | 3/3 |
| L-carnitine bolus 4 g, i.v. | 4/4 | 2/2 |
| L-carnitine bolus 4 g, i.v. + 4 g by infusion in 12 hours | 3/4 | 1/2 |
| acetyl L-carnitine bolus 4 g, i.v. + 4 g by infusion in 12 hours | 2/4 | 0/2 |

| | 2nd series | | |
|---|---|---|---|
| | dead/treated | | |
| | cardiogenic shock | septic shock | hypovolemic shock |
| Controls | 8/8 | 5/5 | — |
| acetyl L-carnitine bolus 4 g, i.v. + 4 g by infusion in 12 hours | 2/13 | 0/2 | 0/1 |

Venous blood samples were drawn from all the patients upon their admission to the intensive care unit and at 3-hours intervals during the subsequent 12 hours. The last samples were not drawn from the control group patients because of patient's death. Succinate and fumarate levels were determined in plasma samples by the gas-liquid chromatography procedure discolsed by Chazmers et al. in "Quantitative extraction and gas liquid chromatographic determination of organic acids in plasma", Analyst (1972) 97, 958–967.

The untreated patients showed a progressively increase in plasma succinate and an attendant decrease in fumarate. Conversely, the acetyl L-carnitine-treated patients showed a progressively diminishing succinate concentration and steady increase in fumarate.

It is neither intended nor necessary to rely on any theoretical interpretation to account for the therapeutical effectiveness of acetyl L-carnitine in reversing shock conditions. However, it may be tentatively hypothesized that succinate dehydrogenase is inhibited in patients in shock conditions, otherwise the increase in succinate and the attendant decrease in fumarate would be hardly accounted for. Most likely, this inhibition is brought about by the building up of oxaloacetate, a metabolite poorly permeable across the inner mitochondrial membrane and which, therefore, would remain sequestered inside the mitochondria.

Oxaloacetate building up would be brought about by the hypoxia-induced poor ATP availability which would inhibit acetyl-CoA synthesis from glucose and fatty acids, substrates which need ATP to be activated in the early steps of their conversion.

Oxaloacetate which, in normal conditions, is cleared by acetyl CoA with attendant citrate formation, would thus accumulate. In the light of the remarkable effect brought about by acetyl L-carnitine administration on plasma succinate and furmarate, acetyl L-carnitine is likely converted to acetyl CoA which would reconstitute oxaloacetate excess, thus restoring succinate dehydrogenase activity.

What is claimed is:

1. A method of treating a human patient in a state of shock which comprises intravenously administrating to the patient a bolus of acetyl L-carnitine or a pharmacologically acceptable salt thereof which is sufficient to reverse in said patient the shock conditions.

2. The method of claim 1, wherein said bolus comprises from about 3 to about 5 grams of acetyl L-carnitine or an equivalent amount of a pharmacologically acceptable salt thereof.

3. The method of claim 1, which comprises, following the administration of said bolus, further administering to said patient via slow infusion in about 12 hours from about 3 to about 5 grams of acetyl L-carnitine or an equivalent amount of a pharmacologically acceptable salt thereof.

* * * * *